US012768726B2

(12) United States Patent
Grass et al.

(10) Patent No.: US 12,768,726 B2
(45) **Date of Patent: *Oct. 20, 2026**

(54) TRACKING SYSTEM AND MARKER DEVICE TO BE TRACKED BY THE TRACKING SYSTEM

(71) Applicant: KONINKLIJKE PHILIPS N.V., Eindhoven (NL)

(72) Inventors: Michael Grass, Buchholz In der Nordheide (DE); Juergen Erwin Rahmer, Hamburg (DE); Bernhard Gleich, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/626,378

(22) Filed: Apr. 4, 2024

(65) Prior Publication Data

US 2024/0264008 A1 Aug. 8, 2024

Related U.S. Application Data

(63) Continuation of application No. 16/708,493, filed on Dec. 10, 2019, now Pat. No. 11,976,985.

(30) Foreign Application Priority Data

Jun. 21, 2019 (EP) .................................... 19181514

(51) Int. Cl.
*A61B 5/00* (2006.01)
*A61B 1/00* (2006.01)
(Continued)

(52) U.S. Cl.
CPC ............ *G01K 7/36* (2013.01); *A61B 1/00158* (2013.01); *A61B 5/0215* (2013.01);
(Continued)

(58) Field of Classification Search
CPC . G01K 7/36; G01K 1/26; G01K 13/04; A61B 1/00158; A61B 5/0215;
(Continued)

(56) References Cited

U.S. PATENT DOCUMENTS 3,456,508 A 7/1969 Frische
6,129,668 A 10/2000 Haynor
(Continued)

FOREIGN PATENT DOCUMENTS

GB 626624 9/1949
WO 03053533 A2 7/2003
(Continued)

OTHER PUBLICATIONS

Maxwell et al."Validation of the Calypso Surface Beacon Transponder" , Journal of Applied Clinical Medical Physics, vol. 17, pp. 223-234 (2016).

(Continued)

*Primary Examiner* — Christopher Koharski
*Assistant Examiner* — James F McDonald, III

(57) ABSTRACT

The invention relates to a marker device and a tracking system for tracking the marker device, wherein the marker device comprises a rotationally oscillatable magnetic object and wherein the rotational oscillation is excitable by an external magnetic field, i.e. a magnetic field which is generated by a magnetic field providing unit 20, 31 that is located outside of the marker device. The rotational oscillation of the magnetic object induces a current in coils, wherein based on these induced currents the position and optionally also the orientation of the marker device is determined. This wireless kind of tracking can be carried out with relatively small marker devices, which can be placed, for instance, in a guidewire, the marker devices can be read out over a relatively large distance and it is possible to use (Continued)

a single marker device for six degrees of freedom localization.

11 Claims, 13 Drawing Sheets

(51) Int. Cl.

| | |
|---|---|
| ***A61B 5/0215*** | (2006.01) |
| ***A61B 5/05*** | (2021.01) |
| ***A61B 5/06*** | (2006.01) |
| ***A61B 34/20*** | (2016.01) |
| ***A61B 90/00*** | (2016.01) |
| ***G01K 1/26*** | (2006.01) |
| ***G01K 7/36*** | (2006.01) |
| ***G01K 13/04*** | (2006.01) |
| ***G01L 9/00*** | (2006.01) |

(52) U.S. Cl.
CPC ............ *A61B 5/02152* (2013.01); *A61B 5/05* (2013.01); *A61B 5/062* (2013.01); *A61B 5/6851* (2013.01); *A61B 5/6852* (2013.01); *A61B 34/20* (2016.02); *A61B 90/36* (2016.02); *A61B 90/39* (2016.02); *G01K 1/26* (2013.01); *G01K 13/04* (2013.01); *G01L 9/0001* (2013.01); *G01L 9/007* (2013.01); *A61B 5/02158* (2013.01); *A61B 2034/2051* (2016.02); *A61B 2034/2072* (2016.02); *A61B 2090/3958* (2016.02); *A61B 2090/3966* (2016.02); *A61B 2562/0223* (2013.01)

(58) Field of Classification Search
CPC ....... A61B 5/02152; A61B 5/05; A61B 5/062; A61B 5/6851; A61B 5/6852; A61B 34/20; A61B 90/36; A61B 90/39; A61B 5/02158; A61B 2034/2051; A61B 2034/2072; A61B 2090/3958; A61B 2090/3966; A61B 2562/0223; A61B 5/03; A61B 5/6853; A61B 5/6862; A61B 2017/00809; A61B 2090/309; A61B 2090/376; A61B 2090/3937; A61B 2090/3954; A61B 2090/3995; A61B 2560/0252; A61B 5/6847; G01L 9/0001; G01L 9/007; G01L 1/10; G01L 19/14; A61M 2025/0166; A61M 25/0127; A61M 25/09041
See application file for complete search history.

(56) References Cited

U.S. PATENT DOCUMENTS

| | | | |
|---|---|---|---|
| 9,071,062 | B2 | 6/2015 | Whitehead |
| 2003/0117269 | A1 | 6/2003 | Dimmer |
| 2004/0138555 | A1 | 7/2004 | Krag |
| 2005/0174109 | A1 | 8/2005 | Pullini |
| 2006/0283007 | A1 | 12/2006 | Cros |
| 2007/0236213 | A1 | 10/2007 | Paden et al. |
| 2008/0001756 | A1 | 1/2008 | Dimmer et al. |
| 2009/0209852 | A1 | 8/2009 | Mate |
| 2009/0278553 | A1 | 11/2009 | Kroh |
| 2010/0276501 | A1 | 11/2010 | Yoshimura |
| 2011/0313415 | A1 | 12/2011 | Fernandez |
| 2015/0126829 | A1 | 5/2015 | Bernstein |
| 2016/0029998 | A1 | 2/2016 | Brister |
| 2016/0261233 | A1 | 9/2016 | Pohl et al. |
| 2017/0084373 | A1 | 3/2017 | Hong |
| 2017/0234741 | A1 | 8/2017 | Erickson et al. |
| 2017/0347913 | A1 | 12/2017 | Isaacson |
| 2018/0078329 | A1 | 3/2018 | Hansen |
| 2019/0022412 | A1 | 1/2019 | Vertatschitsch |
| 2019/0167149 | A1 | 6/2019 | Buesseler |

FOREIGN PATENT DOCUMENTS

| | | | |
|---|---|---|---|
| WO | 2008142629 | A1 | 11/2008 |
| WO | 2019243098 | A1 | 12/2019 |

OTHER PUBLICATIONS

Wilfried, Andra et al."A Novel Method for Real-Time Magnetic Marker Monitoring in the Gastrointestinal Tract", Phys. Med. Biology, vol. 45, 2000, pp. 3081-3093.

TRACKING SYSTEM AND MARKER DEVICE TO BE TRACKED BY THE TRACKING SYSTEM

CROSS-REFERENCE TO PRIOR APPLICATIONS

This application is a Continuation of application Ser. No. 16/708,493, filed Dec. 10, 2019, which claims the benefit of European patent application Ser. No. 19/181,514.1, filed on Jun. 21, 2019. These applications are hereby incorporated by reference herein.

FIELD OF THE INVENTION

The invention relates to a marker device to be tracked, a medical device with the marker device, and a tracking system, tracking method and tracking computer program for tracking the marker device. The invention relates further to a guidance system, a guidance method and a guidance computer program for guiding during a surgical procedure.

BACKGROUND OF THE INVENTION

It is known to track a medical device electromagnetically, especially in minimally invasive medical procedures. This electromagnetic tracking has the disadvantage that, for determining not only the position, but also the orientation, of the medical device, the medical device needs to be equipped with several electromagnetic marker devices, wherein each marker device is adapted for, for instance, a three degrees of freedom (DoF) or five DoF localization. Moreover, the electromagnetic marker devices are significantly larger than 1 mm. For instance, the electromagnetic marker device used by the tracking system disclosed in the article "Validation of the Calypso Surface Beacon Transponder" by B. Maxwell et al., Journal of Applied Clinical Medical Physics, volume 17, pages 223-234 (2016) has a size of 8 mm. Furthermore, electromagnetic marker devices often cannot be read out from a relatively large distance being, for instance, larger than 30 cm. For example, the system disclosed in the above mentioned article by B. Maxwell et al. allows reading out the marker devices from a distance of about 16 cm.

SUMMARY OF THE INVENTION

It is therefore an object of the present invention to provide an improved marker device and an improved tracking system, method and computer program for tracking the marker device. It is a further object of the present invention to provide a medical device with the approved marker device, and a guidance system, method and computer program for guiding during a surgical procedure, which use the marker device and the tracking system.

In a first aspect of the present invention a marker device to be tracked is presented, wherein the marker device comprises a) a casing, b) a magnetic object being arranged within the casing such that it is rotatable out of an equilibrium orientation if an external magnetic torque is acting on the magnetic object, and c) a restoring torque unit being adapted to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque.

Since the magnetic object is arranged within the casing such that it is rotatable out of an equilibrium orientation by an external magnetic torque acting on the magnetic object and since the restoring torque unit is adapted to provide a restoring torque to force the magnetic object back to the equilibrium orientation if the external magnetic torque has rotated the magnetic object out of the equilibrium orientation, in order to allow for a rotational oscillation of the magnetic object excited by the external magnetic torque, induction signals that are caused by the rotational oscillation of the magnetic object and that depend on the spatial position and orientation of the marker device can be generated in an excitation and induction signal unit of a tracking system. In particular, the excitation and induction signal unit can comprise i) first coils adapted to generate the magnetic field providing the magnetic torque for rotating the magnetic object of the tracking device out of its equilibrium orientation and to thereby excite the rotational oscillation of the magnetic object and ii) second coils adapted to generate the induction signals that depend on the spatial position and orientation of the marker device. This allows determining the position and orientation, i.e. six degrees of freedom, of the marker device such that it is possible to determine the position and the orientation of a medical device equipped with this marker device by using only a single marker device. Moreover, the tracking system can read out the marker device from a relatively large distance which is, for instance, larger than 30 cm. Furthermore, the marker device can be relatively small, for instance, smaller than 1 mm. In a preferred embodiment, the casing of the marker device is cylindrical and the outer diameter of the cylinder is smaller than 1 mm, further preferred smaller than 0.5 mm and even further preferred smaller than 0.3 mm.

It is noted that the term "external magnetic torque" refers to a magnetic torque caused by an external magnetic field providing unit being outside of the marker device. Preferentially, the magnetic field providing unit is also outside of a subject, if the marker device is arranged within the subject.

Preferentially, the magnetic object is rotatable around a virtual rotational axis centrally traversing the magnetic object, wherein the magnetic object is rotationally symmetric with respect to the virtual rotational axis. In particular, the magnetic object is a magnetic sphere or a magnetic cylinder. Moreover, the restoring torque unit may comprise a torsional spring mechanism for providing the restoring torque. In addition or alternatively, the restoring torque unit might also comprise a further magnetic object for providing the restoring torque. In an embodiment the magnetic object is attached to one end of a filament, wherein another end of the filament is attached to the casing, wherein the filament is adapted to prevent that the magnetic object touches the further magnetic object due to their magnetic attraction and to allow the magnetic object to rotationally oscillate. The further magnetic object is preferentially stationarily attached to the casing. However, the further magnetic object can also be arranged within the casing such that it is rotationally oscillatable relative to the casing. In particular, the further magnetic object can be attached to one end of a filament, wherein another end of the filament can be attached to the casing. In a preferred embodiment the further magnetic object is rotatable around a virtual rotational axis centrally traversing the further magnetic object, wherein the further magnetic object is rotationally symmetric with respect to the virtual rotational axis. Also the further magnetic object might be a magnetic sphere or a magnetic cylinder. Moreover, the virtual axes of the magnetic object and the further magnetic object are preferentially aligned with each other.

These techniques allow to provide a restoring torque and hence a rotational oscillation of the magnetic object such that the overall marker device can be relatively small, the resonant frequency of the marker device can be provided as desired and the construction of the marker device can still be relatively simple.

In an embodiment the marker device is adapted such that the further magnetic object is rotatable out of an equilibrium orientation if an external magnetic torque is acting on the further magnetic object, wherein the restoring torque unit is adapted to also provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the rotational oscillations of the magnetic object and the further magnetic object have the same resonant frequency and a phase difference of 180 degrees. This reduces, optimally even cancels, the torque on the casing. The restoring torque unit can use the magnetic object for providing the restoring force for the further magnetic object. In particular, in an embodiment the magnetic object forms a first magnetic dipole, the further magnetic object forms a second magnetic dipole, and the magnetic object and the further magnetic object are arranged such that in the equilibrium orientation the first and second magnetic dipoles point in opposite directions. In an embodiment the magnetic object and the further magnetic object are directly connected to each other via a torsion spring such that in this case the restoring torque unit comprises the torsion spring.

Preferentially the magnetic object and/or the further magnetic object is a permanent magnet. Moreover, the casing is preferentially cylindrical. If the casing is cylindrical, it can be relatively easily introduced into a tubular medical device like a guidewire.

Preferentially the marker device is adapted to fulfill at least one condition of a list consisting of i) a Q factor of at least 100, ii) a dynamic dipole moment of at least 0.5 $\mu Am^2$, and iii) a resonant frequency of at least 100 Hz. It has been found that, if at least one of these conditions is fulfilled, the accuracy of determining the position and preferentially also the orientation of the marker device can be further increased.

It is further preferred that the marker device is radiopaque. This allows to visualize the marker device also by using an x-ray imaging system like a computed tomography system, an x-ray fluoroscopy system, an x-ray C-arm system, et cetera.

In a further aspect of the present invention a set of several marker devices is presented, wherein each marker device of the set has radiopaque material, wherein the radiopaque materials and the resonant frequencies of at least two of the marker devices differ from each other. For instance, the radiopaque materials of at least two of the marker devices can differ with respect to the shape. Thus, they can comprise the same kind of radiopaque material, but the shape of the radiopaque material can be different. It is also possible that the shape of the radiopaque material of the at least to different marker devices is the same, but that the radiopaque material itself is different. It is also possible that the shape and the radiopaque material itself, i.e. the kind of material used as the radiopaque material, can differ for at least two of the marker devices. This allows to distinguish marker devices having different resonant frequencies in an x-ray image.

A tracking system for tracking the marker device can be adapted to selectively excite the marker devices and the tracking system can also comprise assignments between indications, which indicate the different marker devices, and their resonant frequencies such that a user like a physician can choose desired marker devices in an x-ray image, whereafter due to the known assignments only the chosen marker devices may be excited and hence only for these marker devices the position and preferentially also the orientation might be determined.

In a further aspect of the present invention a medical device with at least one of the marker devices is presented. In an embodiment the medical device is a catheter, a guidewire or an implant. This allows determining the position and orientation of a medical device like a catheter, a guidewire or an implant in six DoF by using only a single marker device which can be relative small and which allows for relatively high sensitivity with respect to the detection of the position and orientation of the medical device, i.e. the position and orientation of the medical device can be determined from a relative large distance of, for instance, 30 cm or 40 cm.

In a further aspect of the present invention a tracking system for tracking the marker device is presented, wherein the tracking system comprises: i) an excitation and induction signal unit adapted to a) generate a magnetic field providing a magnetic torque for rotating the magnetic object of the marker device out of its equilibrium orientation and for thereby exciting a rotational oscillation of the magnetic object such that it oscillates with a resonant frequency of the rotational oscillation of the magnetic object, and b) generate induction signals that are caused by the rotational oscillation of the magnetic object and that depend on the spatial position and the orientation of the tracking device, ii) a position determination unit adapted to determine the position of the marker device based on the generated induction signals. The excitation and induction signal unit is preferentially adapted such that the induction signals that are caused by the rotational oscillation of the magnetic object and that depend on the spatial position and the orientation of the marker device, depend on the spatial position and the orientation of the marker device with respect to the excitation and induction signal unit.

In an embodiment the excitation and induction signal unit comprises a) first coils adapted to generate the magnetic field providing the magnetic torque for rotating the magnetic object of the marker device out of its equilibrium orientation and to thereby excite the rotational oscillation of the magnetic object and b) second coils adapted to generate the induction signals that depend on the spatial position and the orientation of the marker device, wherein the first and second coils are separated. The first coils and/or the second coils can be arranged in a mat or in a handheld device. The coils can also be arranged in another element like a box.

In a further embodiment the excitation and induction signal unit comprises coils adapted to a) generate the magnetic field providing the magnetic torque for rotating the magnetic object of the marker device out of its equilibrium orientation and to thereby excite the rotational oscillation of the magnetic object and b) generate the induction signals that depend on the spatial position and the orientation of the marker device. Thus, the same coils can be used for generating the magnetic field and for generating the induction signals. Also in this embodiment the coils may be arranged in a mat or in a handheld device. The coils can also be arranged in another element like a box.

Preferentially the excitation and induction signal unit comprises several coils adapted to generate the induction signals, wherein for each coil an induction signal is generated, which depends on the position and orientation of the marker device relative to the respective coil. Moreover, preferentially the position determination unit is adapted to also determine the orientation of the marker device based on the induction signals. In particular, the position determination unit is adapted to determine the position and orientation of the marker device in six DoF.

The tracking system may further comprise a magnetic field generator adapted to generate a spatially inhomogeneous magnetic field, in order to generate a position dependent resonant frequency of the rotational oscillation of the magnetic object of the marker device, wherein the position determination unit is adapted to determine the position of the marker device also based on the position dependent resonant frequency. In particular, the magnetic field generator is adapted to generate a magnetic field gradient as the spatially inhomogeneous magnetic field. The magnetic field generator may comprise two sets of saddle coils and a split solenoid coil for generating the spatially inhomogeneous field. This allows for a further improved determination of the position of the marker device. However, other coil configurations which generate the inhomogenous field can of course also be used.

Preferentially the tracking system is adapted to determine the position of several marker devices, wherein the magnetic objects of the several marker devices are rotationally oscillatable with different resonant frequencies such that the induction signals of different marker devices have different frequencies, wherein the position determination unit is adapted to determine the positions of the marker devices based on the generated induction signals having the different frequencies. The position determination unit is preferentially also adapted to determine the orientation of the marker devices based on the generated induction signals having the different frequencies. By using the different marker devices with different resonant frequencies, it is possible to distinguish between different marker devices and to determine, for each marker device, the respective position and preferentially also the respective orientation.

The several marker devices can be attached to an element, wherein the position determination unit can be adapted to determine the shape of the element based on the determined positions of the several marker devices. The shape determination unit can be adapted to determine the shape of the element also based on orientations determined for the several marker devices. The element is preferentially a medical device, but it can also be a body part like tissue.

In an embodiment the position determination unit is adapted to determine the position of the marker device relative to a position of another marker device. Also, the orientation of the marker device can be determined relative to the orientation of another marker device. However, the position and optionally also the orientation can also be determined relative to another reference.

Moreover, an output unit can be provided for outputting the determined position of the marker device. The output unit can also be adapted to output the orientation of the marker device.

In an embodiment the marker device is located within a subject, wherein the position determination unit is adapted to determine a nearest position on a surface of the subject, which is the position on the surface of the subject being nearest to the position of the marker device, and/or a projection of the position of the marker device on the surface of the subject in a predefined direction. For instance, the output unit can comprise a light source like a light-emitting diode or a laser and light generated by the light source can be used for generating a light point on the surface of the object at the determined nearest position and/or at the determined position on the surface to which the determined position of the marker device has been projected. Particularly, in this example, the tracking system might at least be partly integrated in a hand-held device comprising the light source such that, if the hand-held device is held in front of the patient, the hand-held device can generate a light point at the respective position on the surface of the subject. In a preferred embodiment the position determination unit is adapted to determine a distance between the determined position on the surface of the subject and the position of the marker device. The distance preferentially corresponds to the depth within the subject in a normal direction or along the predefined direction. The distance might be indicated by a corresponding number. However, in addition or alternatively, it is also possible to indicate the distance by generating the light point, if a light source is used for indicating the determined position on the surface, depending on the distance. For instance, the color, the shape and/or the size of the light point can depend on the determined distance. The predefined direction can be, for instance, the x-ray projection direction of an x-ray imaging system like a C-arm x-ray imaging system, the normal direction of the hand-held device, et cetera.

The tracking system and the marker device are preferentially adapted such that the magnetic object of the marker device rotationally oscillates over an angular range of at least 30 degrees.

In a further aspect of the present invention a guidance system for guiding during a surgical procedure is presented, wherein the guidance system comprises the tracking system for tracking the position of the marker device and an output unit adapted to output the tracked position.

The tracking system can be adapted to track the orientation of the marker device, wherein the output unit can be adapted to also output the tracked orientation of the marker device. The target is, for instance, a tumor such that the tumor can be found relatively easily within the subject during the surgical procedure by tracking the marker device.

Preferentially the guidance system further comprises an imaging system adapted to generate an image of a subject to whom the surgical procedure is applied, wherein the tracking system is registered with the imaging system and wherein the output unit is adapted to overlay at least the tracked position with the image of the subject. This can lead to a further improved guidance of, for instance, a physician during a surgical procedure to be applied to the target to which the marker device has been attached.

In an embodiment the marker device is located within a subject, wherein the output unit is adapted to indicate the determined nearest position on the surface of the subject and/or a distance between the marker device and this determined nearest position.

In another aspect a tracking method for tracking the marker device is presented, wherein the tracking method comprises a) generating a magnetic field providing a magnetic torque for rotating the magnetic object of the marker device out of its equilibrium orientation and for thereby exciting a rotational oscillation of the magnetic object such that it oscillates with a resonant frequency of the rotational oscillation of the magnetic object, and generating induction signals that are caused by the rotational oscillation of the magnetic object and that depend on the spatial position and the orientation of the tracking device, and b) determining the position of the marker device based on the generated induction signals.

In a further aspect a guidance method for guiding during a surgical procedure by using the guidance system is presented, wherein the guidance method comprises tracking the position of the marker device as defined by the tracking method and outputting the tracked position.

In another aspect of the present invention a tracking computer program for tracking the marker device is presented, wherein the computer program comprises program code means for causing the tracking system to carry out the steps of the tracking method, when the computer program is run on a computer controlling the tracking system.

In a further aspect of the present invention a guidance computer program for guiding during a surgical procedure is presented, wherein the computer program comprises program code means for causing the guidance system to carry out the steps of the guidance method, when the computer program is run on a computer controlling the guidance system.

It shall be understood that the marker device, the set of marker devices, the tracking system, the guidance system, the tracking method, the guidance method, the tracking computer program and the guidance computer program as described herein have similar and/or identical preferred embodiments, in particular, as defined above and/or in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
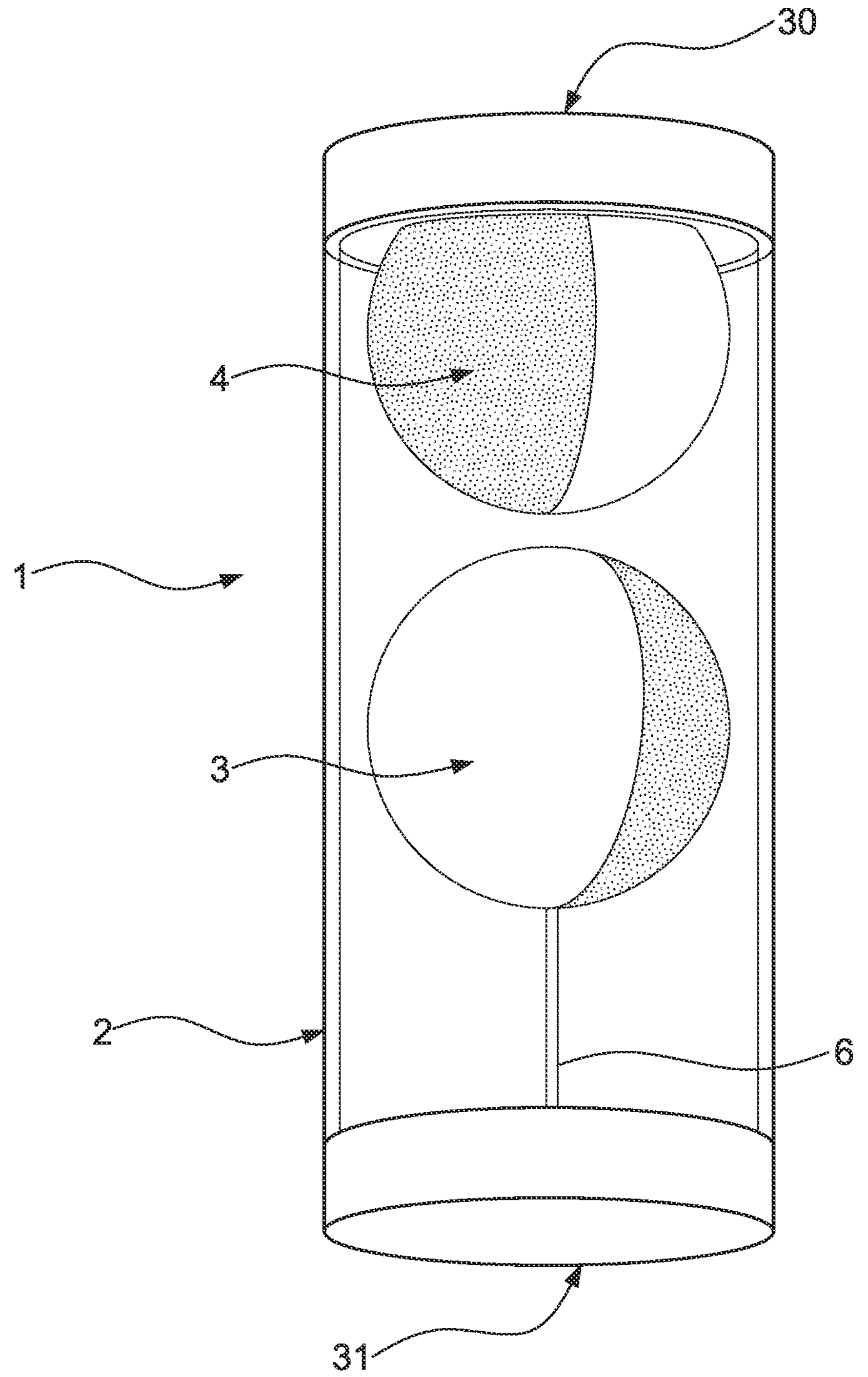
FIGS. 1 to 5 show schematically and exemplarily different embodiments of a marker device to be tracked.

FIG. 1 shows schematically and exemplarily an embodiment of a marker device to be tracked by using a tracking system. The marker device 1 comprises a casing 2 and a magnetic object 3 being arranged within the casing 2 such that it is rotatable out of an equilibrium orientation if an external magnetic torque is acting on the magnetic object 3. The marker device 1 further comprises a restoring torque unit 4 being adapted to provide a restoring torque to force the magnetic object 3 back into the equilibrium orientation if an external magnetic force has rotated the magnetic object 3 out of the equilibrium orientation, in order to allow for a rotational oscillation of the magnetic object 3 excited be the external magnetic torque. In this embodiment the casing 2 is cylindrical and the magnetic object 3 is rotatable around a virtual rotational axis centrally traversing the magnetic object 3, wherein the magnetic object 3 is rotationally symmetric with respect to the virtual rotational axis. In particular, in this embodiment the magnetic object 3 is a magnetic sphere.

The restoring torque unit 4 comprises a further magnetic object 4 for providing the restoring torque. In particular, the magnetic object 3 is attached to one end of a filament 6, wherein another end of the filament 6 is attached to the casing 2. The filament 6 is adapted to prevent the magnetic object 3 from touching the further magnetic object 4 due to their magnetic attraction and to allow the magnetic object 3 to rotationally oscillate. In this embodiment the further magnetic object 4 is stationarily attached to the casing 2.

The magnetic object 3 forms a first magnetic dipole, the further magnetic object 4 forms a second magnetic dipole and the magnetic object 3 and the further magnetic object 4 are arranged such that in the equilibrium orientation the first and second magnetic dipoles point in opposite directions. Preferentially, the first magnetic object 3 and the second magnetic object 4 are permanent magnets, wherein in the equilibrium orientation a north pole of the magnetic object 3 faces a south pole of the further magnetic object 4 and vice versa.

The casing 2 is cylindrical, wherein the cylindrical casing 2 comprises two end surfaces 30, 31 and wherein the further object 4 is stationarily attached to a first end surface 30 and the end of the filament 6, which is opposite to the end attached to the magnetic object 3, is attached to the second end surface 31 of the cylindrical casing 2.

Figure 2:
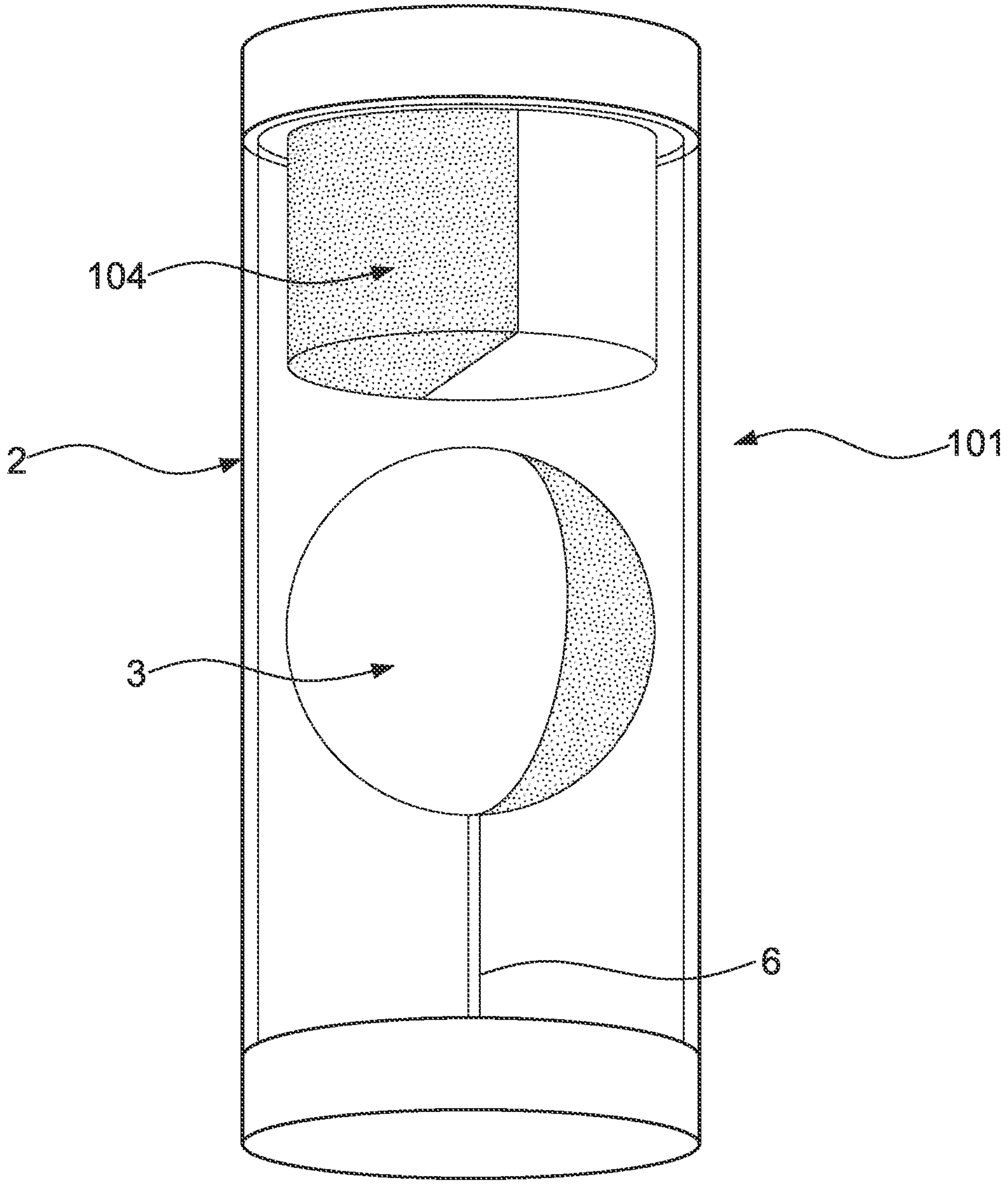

FIG. 2 shows schematically and exemplarily a further embodiment of a marker device 101 to be tracked by the tracking system. The marker device 101 is similar to the marker device 1 schematically and exemplarily illustrated in FIG. 1 with the difference that the further magnetic object 104 of the marker device 101 is cylindrical and the further magnetic object 4 of the marker device 1 is spherical.

Figure 3:
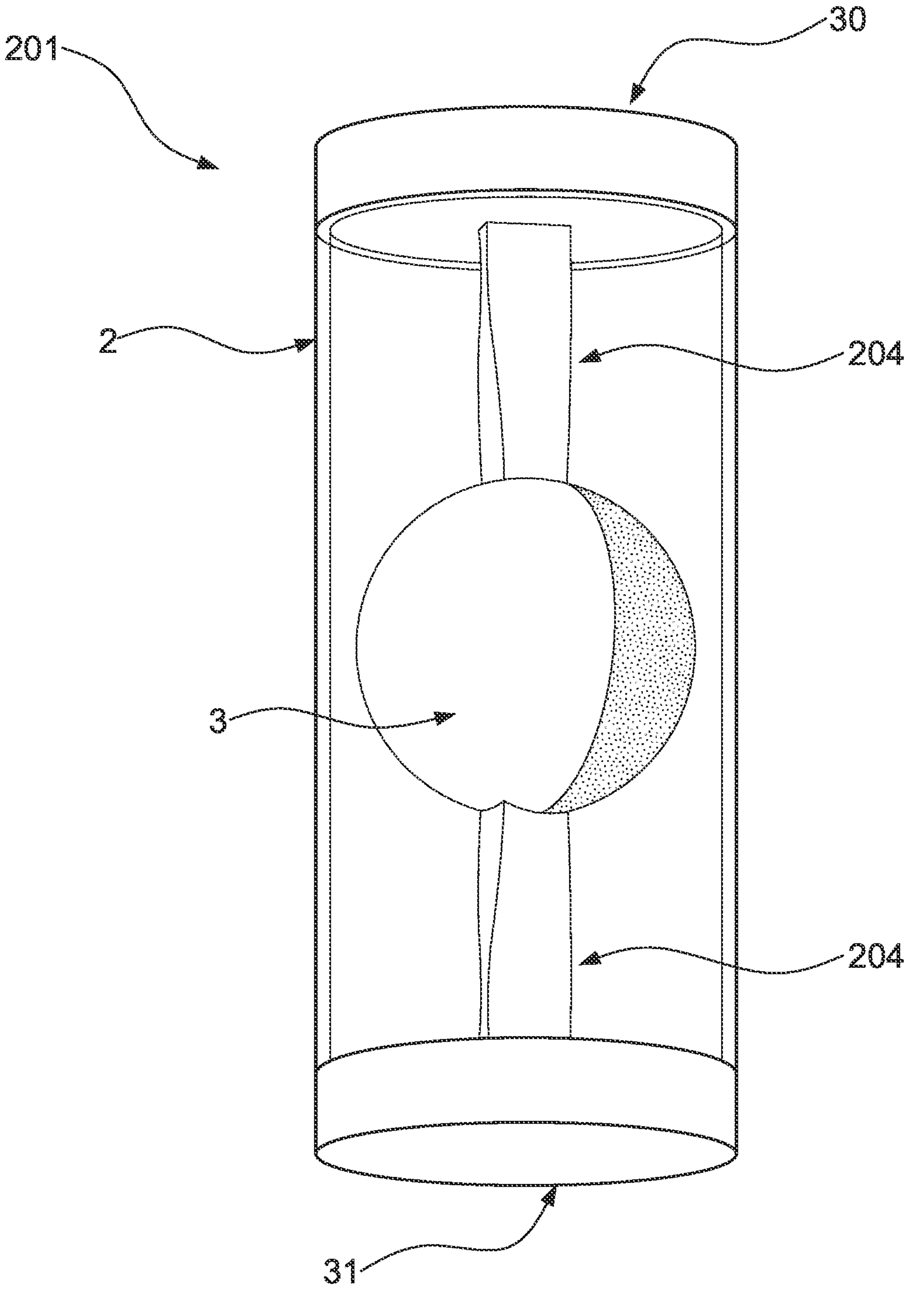

A further embodiment of a marker device 201 to be tracked by using the tracking system is schematically and exemplarily illustrated in FIG. 3. Also in this embodiment the marker device 201 comprises a cylindrical casing 2 and a spherical magnetic object 3 being arranged within the casing 2 such that it is rotatable out of an equilibrium orientation if an external magnetic torque is acting on the magnetic object 3. However, in this embodiment the restoring torque unit differs from the restoring torque unit described above with reference to FIG. 1.

The restoring torque unit 204 of the marker device 201 is also adapted to provide a restoring torque to force the magnetic object 3 back into the equilibrium orientation if an external magnetic force has rotated the magnetic object 3 out of the equilibrium orientation, in order to allow for a rotational oscillation of the magnetic object 3 excited by the external magnetic torque. Moreover, also in this embodiment the magnetic object 3 is rotatable around a virtual rotational axis centrally traversing the magnetic object 3, wherein the magnetic object 3 is rotationally symmetric with respect to the virtual rotational axis. In particular, also in this embodiment the magnetic object 3 is a magnetic sphere. However, the restoring torque unit 204 comprises a torsional spring mechanism for providing the restoring torque. In particular, the torsional spring mechanism comprises two torsional springs 204, wherein one of these torsional springs 204 attaches the magnetic sphere with the first end surface 30 of the cylindrical casing 2 and the other torsional spring 204 attaches the magnetic sphere 3 to the second end surface 31 of the cylindrical casing 2.

Figure 4:
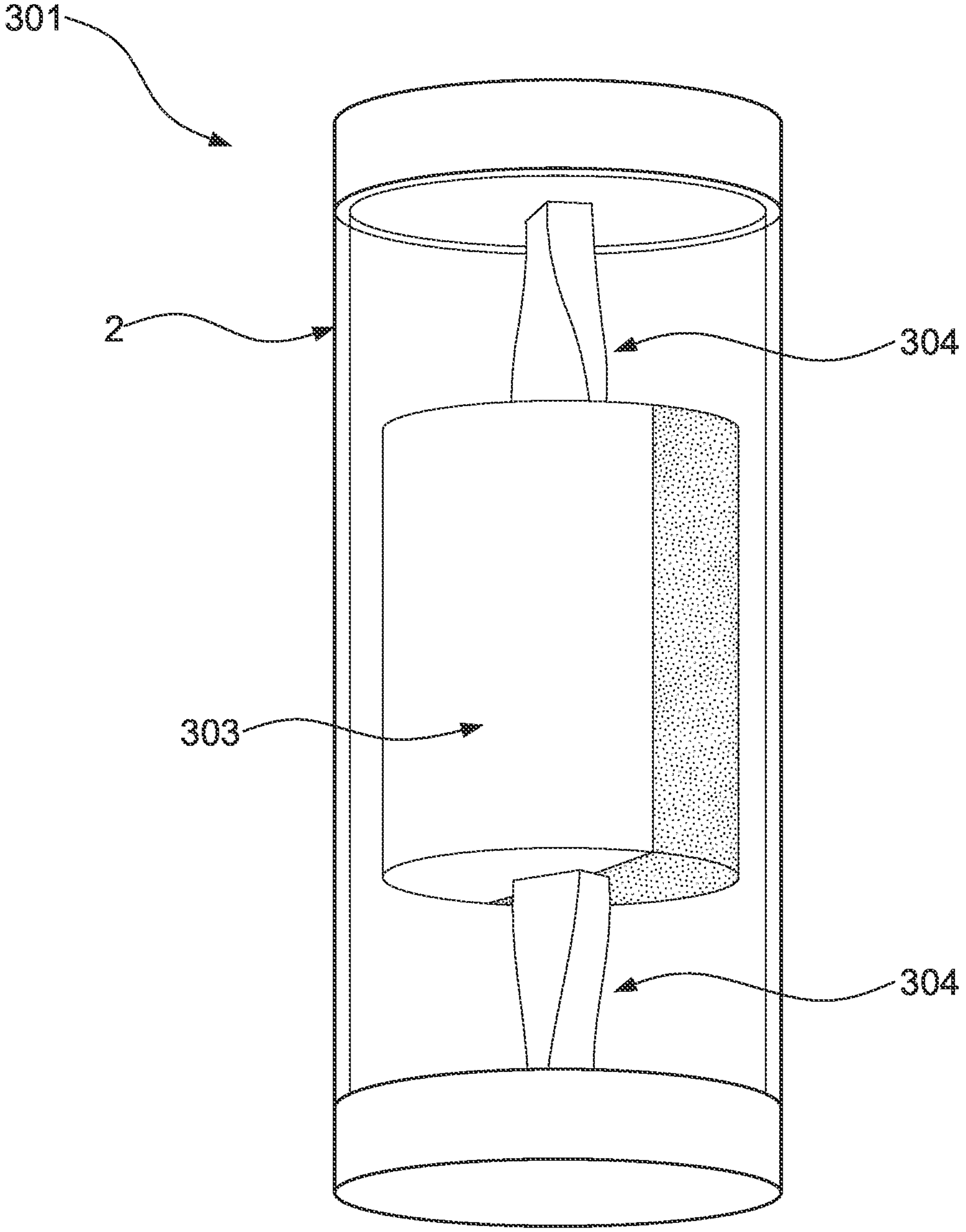

FIG. 4 shows schematically and exemplarily a further embodiment of a marker device 301 to be tracked by the tracking system, which is similar to the marker device 201 described above with FIG. 3 with the difference that the marker device 301 comprises a cylindrical magnetic object 303, whereas the marker device 201 comprises a spherical magnetic object 3. Moreover, the torsional springs 304 of the marker device 301 for providing the torsional spring mechanism are shorter than the torsional springs 204 of the marker device 201.

Figure 5:
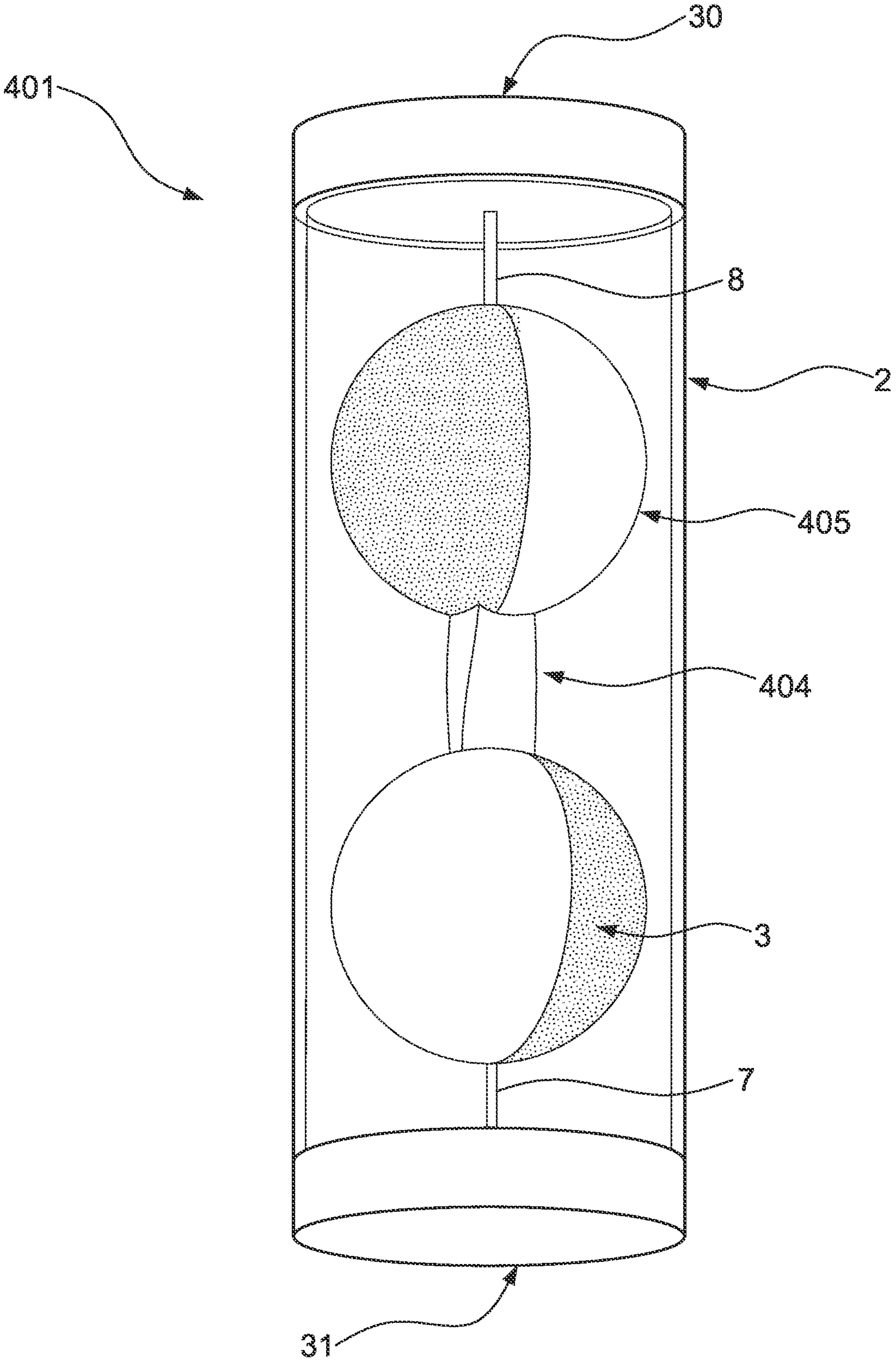

A further embodiment of the marker device 401 to be tracked by using the tracking system is schematically and exemplarily illustrated in FIG. 5. The marker device 401 also comprises a cylindrical casing 2 and a magnetic object 3 being arranged within the casing 2 such that it is rotatable out of an equilibrium orientation if an external magnetic torque is acting on the magnetic object 3. Moreover, also in this embodiment the magnetic object 3 is a magnetic sphere and it is attached to one of two end surfaces 30, 31 via a filament 7. Furthermore, also the marker device 401 comprises a restoring torque unit 404, 405 being adapted to provide a restoring torque to force the magnetic object 3 back into the equilibrium orientation if an external magnetic torque has rotated the magnetic object 3 out of the equilibrium orientation, in order to allow for a rotational oscillation of the magnetic object 3 excited by the external magnetic torque. Moreover, also in this embodiment the magnetic object 3 is rotatable around a virtual rotational axis centrally traversing the magnetic object 3, wherein the magnetic object 3, being a magnetic sphere in this embodiment, is of course rotationally symmetric with respect to the virtual rotational axis.

Also in this embodiment the restoring torque unit comprises a torsional spring mechanism 404 for providing the restoring torque, wherein in this embodiment the torsional spring mechanism 404 is provided by a torsional spring connecting the magnetic object 3 and a further magnetic object 405 to each other. Moreover, the restoring torque unit can be regarded as also comprising the further magnetic object 405 for providing the restoring torque, wherein the further magnetic object 405 is also a magnetic sphere. The further magnetic object 405 is arranged within the casing such that it is rotationally oscillatable relative to the casing 2, wherein the further magnetic object 405 is rotatable around a virtual rotational axis centrally traversing the further magnetic object 405. The virtual axes of the magnetic object 3 and the further magnetic object 405, along which the magnetic object 3 and the further magnetic object 405, respectively, are rotatable, are aligned with each other. Moreover, the further magnetic object 405 is attached to one end of a filament 8, wherein another end of the filament 8 is attached to the other of the two end surfaces 30, 31 of the cylindrical casing 2.

Figure 6:
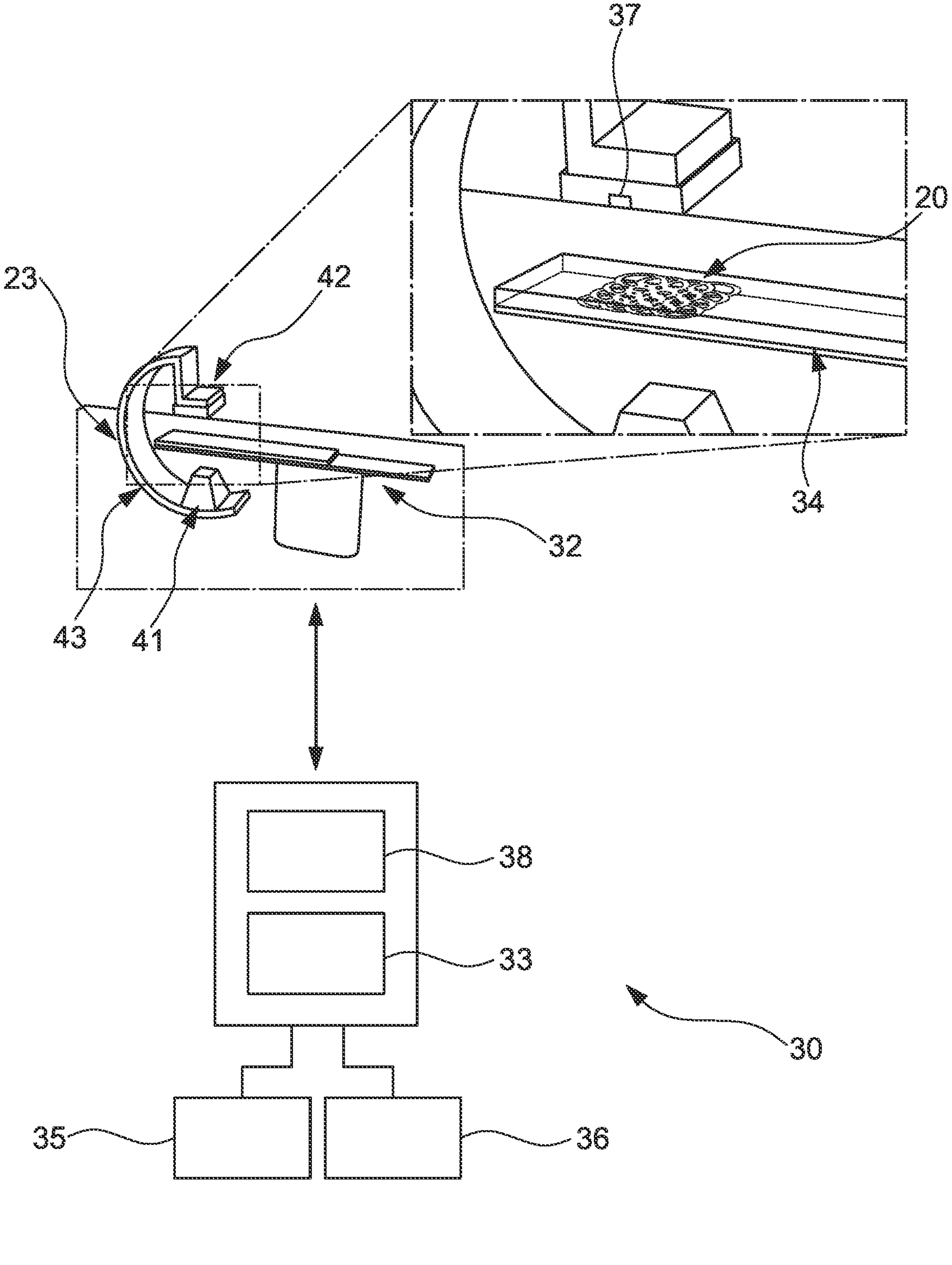
FIG. 6 shows schematically and exemplarily an embodiment of a guidance system for guiding a physician during a surgical procedure, which includes a tracking system for tracking the marker devices schematically and exemplarily shown in FIGS. 1 to 5.

FIG. 6 shows schematically and exemplarily an embodiment of a guidance system 30 for guiding during a surgical procedure. The guiding system comprises an imaging system 23 adapted to generate an image of a subject who is arranged on a support means 32 like a patient table and to whom the surgical procedure is applied. In this embodiment the imaging system 23 is a C-arm imaging system for generating two-dimensional and/or three-dimensional images of the subject. The C-arm system 23 comprises an x-ray source 41 and an x-ray detector 42 attached to opposing ends of a C-like support structure 43.

The guidance system 30 further comprises a tracking system for tracking the position of the marker device 1 or of any other of the above described marker devices 101, 201, 301, 401 while the marker device is attached to an object to be tracked. The object to be tracked is, for instance, a lesion within the subject and/or a medical device to be moved within the subject. In particular, several marker devices can be attached to one or several inner parts of the subject and/or to one or several medical devices to be moved within the subject, in order to track the positions of these objects and allow for, for instance, a guidance of a medical device to a lesion within the subject. However, it is also possible that the tracking system only tracks the position of a medical device while being moved within the subject or that the tracking system just tracks the position of an inner part of the subject like a lesion.

The imaging system 23 and the tracking system are registered with each other such that an output unit 36 like a monitor can output and overlay at least the tracked position of, for instance, a lesion and/or of a medical device within the subject with an image of the subject generated by using the imaging system 23.

The tracking system comprises coils 20 adapted to a) generate a magnetic field providing a magnetic torque for rotating the magnetic object 3 of the marker device 1 out of its equilibrium orientation and to thereby excite the rotation oscillation of the magnetic object 3 and b) generate induction signals that depend on the spatial position and the orientation of the marker device 1. The tracking system further comprises a tracking control unit 31 being configured to control the coils 20 by providing and controlling the current for the coils 20 such that the desired magnetic field is generated and to generate digital induction signals being indicative of the induction influences on the currents within the coils 20 caused by the rotational oscillation of the marker device 1. The coils 20 and the tracking control unit 31 magnetically excite the marker device 1 and generate an induction signal such that the coils 20 and the tracking control unit 31 can be regarded as forming an excitation and induction signal unit 20, 31.

In this embodiment the coils 20 are arranged in a mat 34 on the support means being, in this example, a patient table. However, the coils 20 could also be arranged in or at another part of the tracking system. For instance, the coils 20 may also be arranged in a handheld device such that the tracking system could be carried in a hand. In this case preferentially a further tracking system is used for tracking the position and the orientation of the handheld device relative to the position and orientation of the imaging system 23, in order to register the tracking system with the imaging system 23. For this tracking known tracking systems like optical tracking systems or other tracking systems could be used.

Although in this embodiment the same coils 20 are used for generating the magnetic field and for generating the induction signals, in other embodiments it is also possible that a) first coils are used for generating the magnetic field providing the magnet torque for rotating the magnetic object 3 of the marker device 1 out of its equilibrium orientation and for thereby exciting the rotational oscillation of the magnetic object 3 and b) second coils are used for generating the induction signals that depend on the spatial position and the orientation of the marker device, wherein the first and second coils are separated. Also the first coils and/or the second coils can be arranged in a mat or in a handheld device.

For each coil an induction signal is generated, which depends on the position and orientation of the marker device 1 relative to the respective coil, wherein a position determination unit 33 of the tracking system is adapted to determine the position and the orientation of the marker device 1 based on these induction signals. For instance, in a calibration procedure for each position and orientation of the marker device relative to the coils 20 the induction signals can be generated and these induction signals or at least characteristics of these induction signals can be stored. After this calibration has been completed, the position determination unit can use the stored induction signals or the stored characteristics of the induction signals for determining the position and orientation of the marker device based on currently generated induction signals and the stored information. The position determination unit can of course also be adapted to determine the position and orientation of the marker device 1 depending on the induction signals in another way, for instance, based on analytical models, especially functions, which are based on physical considerations and which provide the position and orientation of the marker device as an output if as an input the induction signals are given. It is also possible to use artificial intelligence like a neural network for providing the position and orientation of the marker device depending on the induction signals, wherein the artificial intelligence can be trained by using the stored calibration information.

Although in this embodiment the position determination unit 33 adapted to determine not only the position of the marker device, but also the orientation of the marker device, in another embodiment the position determination unit can be adapted to determine only the position of the marker device or only the orientation of the marker device. However, preferentially the position determination unit 33 is adapted to determine the position and orientation of the marker device 1 in six DoF.

The position determination unit 33 can be adapted to determine a nearest position on a surface of the subject, which is the position on the surface of the subject being nearest to the position of the marker device 1. In particular, the position determination unit 33 can be adapted to determine the distance between the nearest position on the surface of the subject and the position of the marker device 1, wherein this nearest position on the surface of the subject may be shown on the monitor 36 or it may be directly shown on the skin of the subject. For instance, a light source like a light-emitting diode or a laser 37 may be used for generating a light spot on the subject at the determined nearest position. The light source 37, which might be regarded as being a further output unit of the tracking system, can be arranged, for instance, at the imaging system 23, in a handheld device which might also include coils for generating the magnetic field and/or coils to be used for generating the induction signals, or in another part of the overall system. The position and orientation of the light source 37 is also registered with the tracking system.

The tracking system and the marker device 1 are preferentially adapted such that the magnetic object 3 rotationally oscillates over an angular range of at least 30 degrees. The tracking system can be adapted to determine the position and orientation of several marker devices 1, wherein the magnetic objects 3 of the several marker devices 1 are rotationally oscillatable with different resonant frequencies such that the induction signals of different marker devices 1 have different frequencies and wherein these different frequencies are used by the position determination unit 33 to determine the positions and the orientations of the maker devices 1 based on the generated induction signals having these different frequencies.

Figure 7:
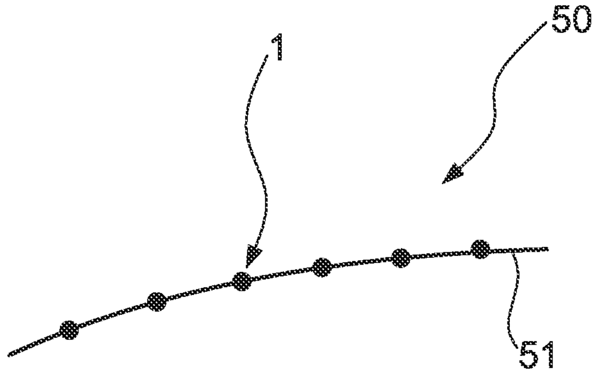
FIG. 7 shows schematically and exemplarily an embodiment of a medical device being a guidewire with several marker devices.

In an embodiment the several marker devices 1 are attached to a medical instrument 51 like a guidewire or a catheter device, in order to provide a medical device 50 being trackable by the tracking system. Such a medical device 50 is schematically and exemplarily illustrated in FIG. 7. The position determination unit 33 can be adapted to determine the positions and orientations of the several marker devices 1 arranged along the length of the elongated medical device 50 and to determine the shape of the medical device 50 based on these determined positions and orientations.

In an embodiment the tracking system can further comprise a magnetic field generator 21 which might be attached to the support means 32 or arranged in another way close to the subject to be treated. The magnet field generator 21 is adapted to generate a spatially inhomogeneous magnetic field, in order to generate a position dependent resonant frequency of the rotational oscillation of the magnetic object 3 of the marker device 1, wherein the position determination unit 33 can be adapted to determine the position of the marker device 1 also based on the position dependent resonant frequency. In particular, the magnetic field generator 21 is adapted to generate a magnetic field gradient as the spatially inhomogeneous magnetic field. In this example the magnetic field generator 21 comprises two sets of saddle coils and a split solenoid coil for generating the spatially inhomogeneous field. Also these coils might be controlled by the tracking control unit 31.

Figure 9:
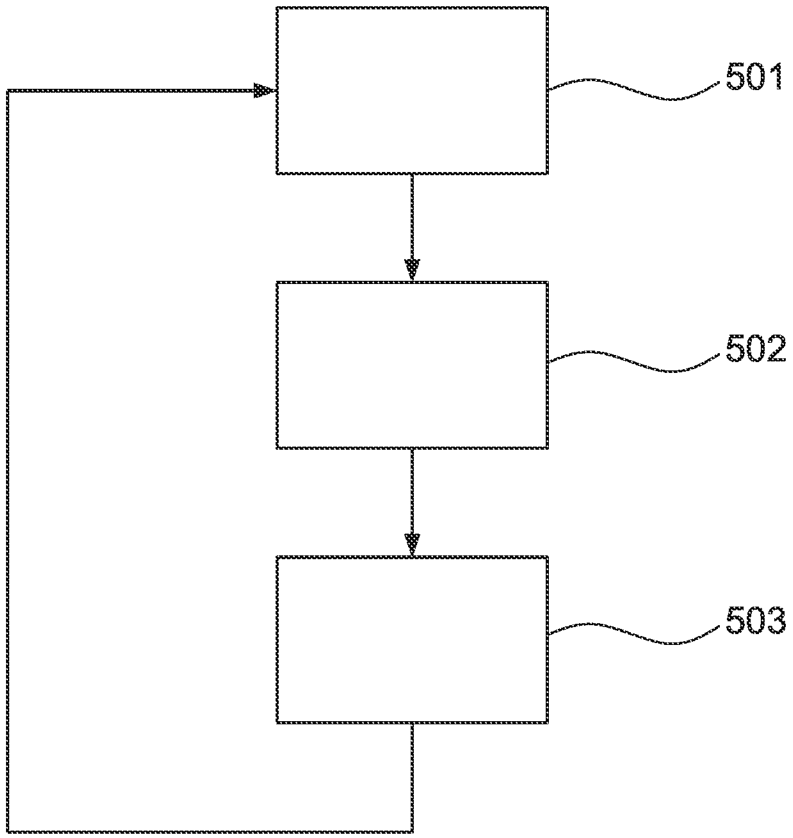
FIG. 9 shows a flowchart exemplarily illustrating an embodiment of a guidance method for guiding a physician during a surgical procedure.

In the following an embodiment of a guidance method for guiding during a surgical procedure by using the guidance system will exemplarily be described with reference to a flowchart shown in FIG. 9.

In step 501 a magnetic field is generated, which provides a magnetic torque for rotating the magnetic object 3 of the marker device 1 within the subject out of its equilibrium orientation and for thereby exciting a rotational oscillation of the magnetic object 3 such that it oscillates with the resonant frequency of the rotational oscillation of the magnetic object 3. Moreover, in step 501 induction signals are generated, which are caused by the rotational oscillation of the magnetic object 3 and which depend on the spatial position and the orientation of the tracking device relative to the coils 20. In step 502 the position of the marker device 1 is determined based on the generated induction signals and in step 503 the determined position is outputted.

Figure 8:
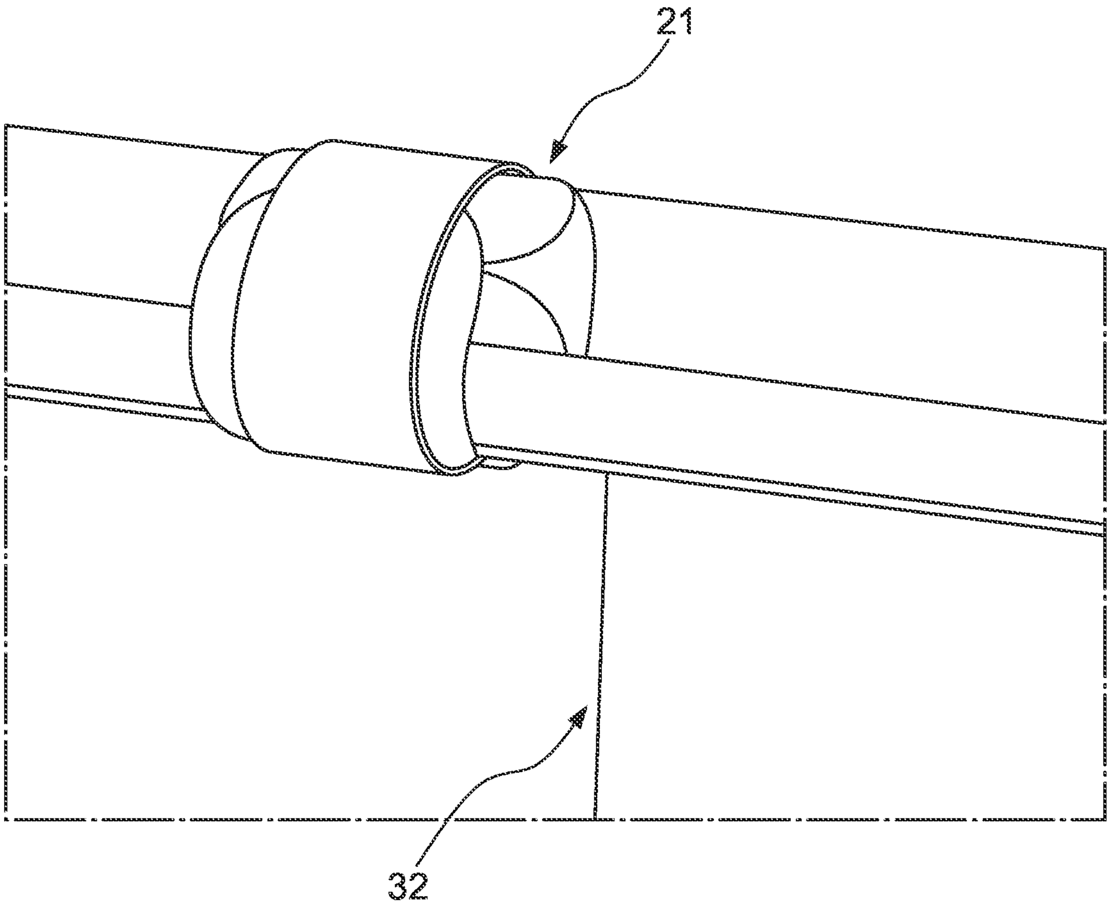
FIG. 8 shows schematically and exemplarily an embodiment of a magnetic field generator for generating a spatially inhomogeneous magnetic field.

Steps 501 to 503 are carried out in a loop such that substantially continuously the position of the marker device can be tracked and output to, for instance, a physician performing the surgical procedure, until the tracking of the position is aborted by, for example, the physician. In particular, the physician might indicate via an input unit 35 like a keyboard, a touchpad, a specific button of the system, et cetera that the tracking should be aborted. Steps 501 and 502, which only relate to the tracking, could also be regarded as being steps of a tracking method for tracking a marker device. The tracking method and the tracking system can also be adapted to determine the position and optionally also the orientation of the marker device at one point in time, i.e. they can be adapted to not determine the position and optionally the orientation over time. However, preferentially the tracking method and the tracking system are adapted to determine the position and optionally the orientation over time It is known to apply electromagnetic (EM) localization in three-dimensional tracking of medical devices in minimally invasive medical procedures or for detecting target motion during external beam radiation therapy (EBRT). For obtaining not only the position, but also the orientation of a tracked medical device, i.e. for tracking the medical device in 6 DoF, the medical device is typically equipped with several 3 or 5 DoF EM markers. In contrast to this, the marker devices described above especially with reference to FIGS. 1 to 5 and the above described tracking system enable wireless 6 DoF detection, i.e. of the three-dimensional position and of three orientation angles, by using a single marker device. The marker devices can be of sub-millimeter size and they can be read out from distances up to, for instance, 30 to 40 cm. As also described above especially with reference to FIG. 8, an additional spatial encoding scheme can provide independent position information for a further increased localization accuracy. Moreover, several marker devices can be detected in parallel, i.e. the position and orientation of several marker devices can be detected in parallel.

A single one of the marker devices described above suffices to obtain full position and full orientation information in space, whereas conventional EM localization requires at least two marker devices, i.e. at least two coils, in or attached to a medical device, in order to obtain, besides full position information, full orientation information. Moreover, the tracking system described above with reference to, for instance, FIG. 6 allows to combine two independent localization approaches, i.e., for instance, localizing by using the coils 20 and also localizing by using the coils 21. Moreover, as disclosed in the above mentioned article by B. Maxwell et al., conventional wireless EM marker devices are substantially larger than 1 mm, i.e., for example, they have a diameter of about 8 mm, whereas the marker devices described above especially with reference to FIGS. 1 to 5 have sub-millimeter sizes.

Furthermore, since the marker devices preferentially use permanent magnets, the marker devices are more sensitive than conventional EM marker devices and thus can be read out from a large distance, i.e., for instance, from a distance being larger than 30 cm. Conventional EM tracking systems with wireless EM marker devices have smaller work spaces, i.e., for example, the wireless EM marker devices disclosed in the above mentioned article by B. Maxwell et al. can be read out from a distance of about 16 cm only.

The marker devices can be regarded as being magnetic micro markers which can be adapted to be operated at different frequencies for making them distinguishable. The tracking system comprises a coil array, i.e. the coils 20, for wireless marker excitation, signal reception and localization. Six DoF localization is feasible by using, for instance, the known spatial coil sensitivity maps of the elements of the coil array, i.e. of the coils 20 shown in FIG. 6. For increasing the spatial accuracy, the tracking system and the tracking method can also use the above described independent spatial encoding that is based on a position dependent frequency variation generated by superposition of a low-frequency inhomogeneous field by using, for instance, a field gradient generator as described above with reference to FIG. 8.

The marker device can comprise a permanent magnet, which might be spherical in shape, which is attached to a filament and which is free to perform a rotational oscillation around an equilibrium orientation determined by a field of a fixed magnet as described above with reference to FIGS. 1 and 2 and which could also be several magnets. It is also possible that a marker device comprises a permanent magnet connected to a torsional spring mechanism which provides the restoring force for a resonant torsional oscillation as described above with reference to FIGS. 3 to 5. Moreover, a cylinder-shaped magnet can be used, in order to maximize the magnetic moment within a cylindrical container, i.e. within the cylindrical casing, as described above with reference to FIG. 4. Furthermore, in order to decouple the oscillation from the outer cylinder and environment, the marker device can also use a spring-based counter-oscillation of two spheres that are connected to the housing, i.e. to the casing, with filaments, for instance, as described above with reference to FIG. 5. In contrast to the marker devices described above with reference to FIGS. 1 to 4, by using a spring-based counter oscillation of two spheres, no or only little torque is exerted on the casing, thus giving a vibrational decoupling from the surrounding. The central torsion spring 404 shown in FIG. 5 increases the resonant frequency in comparison to not using such a central torsion spring. However, it is also possible to remove the torsion spring 404, if lower frequencies are sufficient.

The coil array 20 described above with reference to FIG. 6 provides 6 DoF localization information via the spatial sensitivity profiles of the individual coil elements of the coil array 20. The additional coil system 21 described above with reference to FIG. 8 can be used to create spatially inhomogeneous localization fields that provide independent localization information that can be used to improve localization accuracy if necessary. This active spatial encoding can be provided by two sets of saddle coils and a split solenoid coil.

Figure 10:
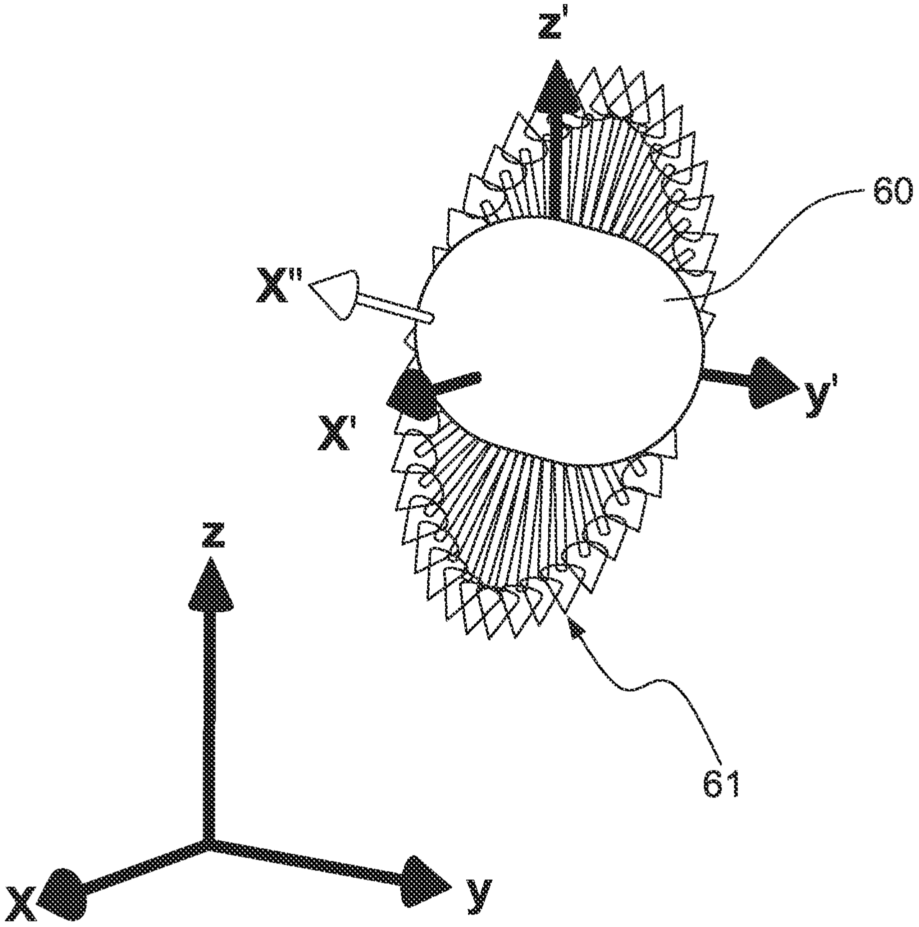
FIGS. 10 to 12 illustrate schematically and exemplarily a six DoF localization of a marker device.
Figure 11:
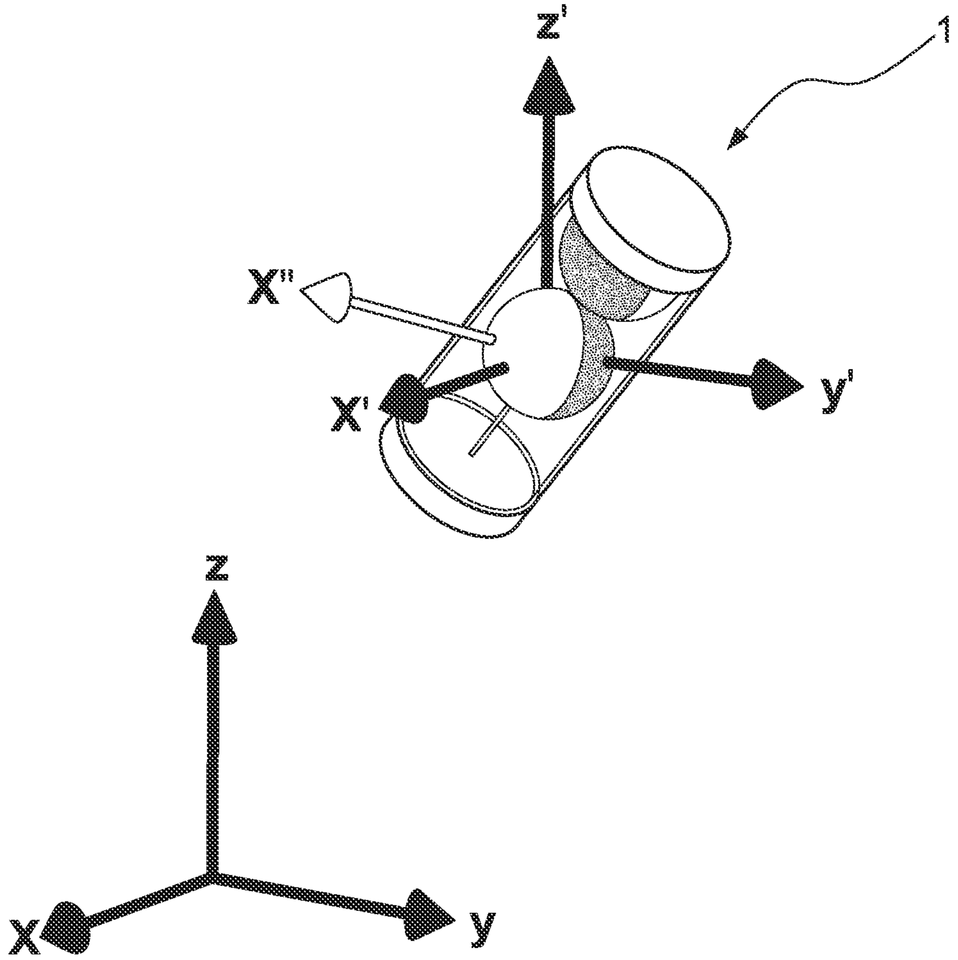
Figure 12:
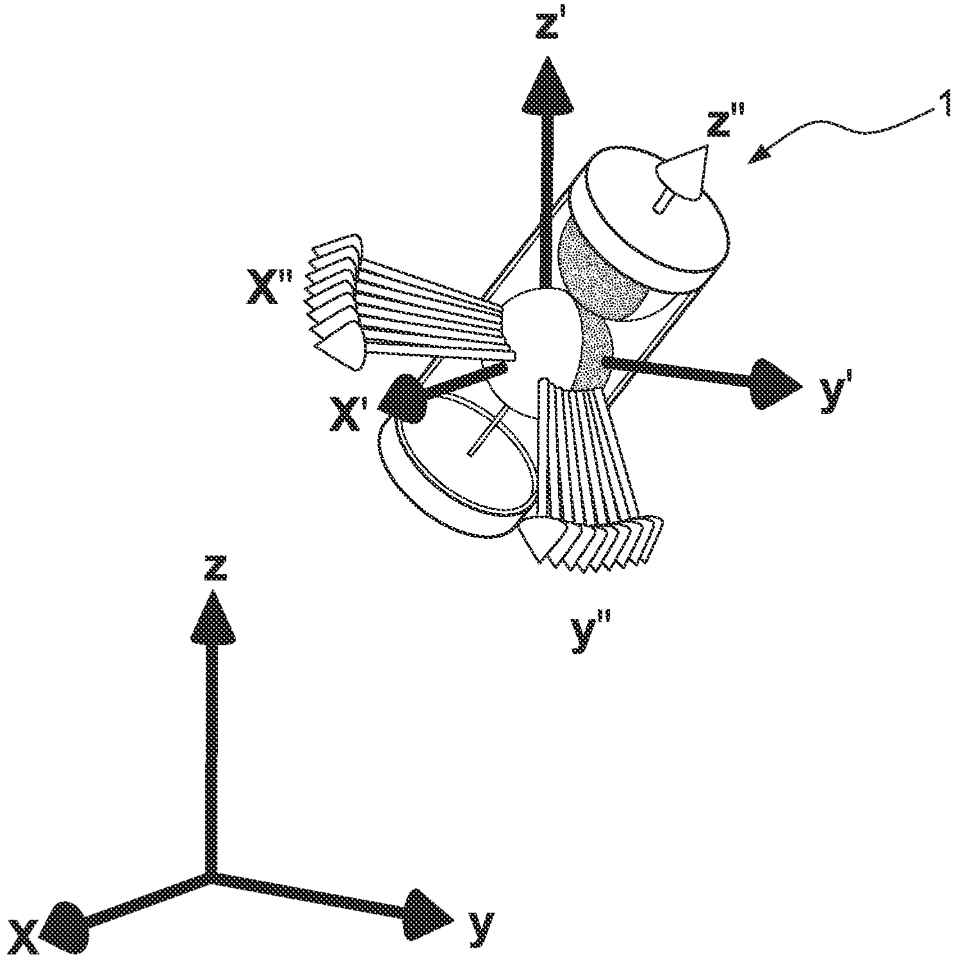

FIGS. 10 to 12 illustrate the six DoF localization enabled by using a rotating permanent magnet like the magnet 3 of the marker device 1. FIG. 10 shows a dipole field characteristic being rotationally symmetric as shown by the iso-surface plot 60 of the field strength. Thus, by measuring the dipole field, the marker device position and orientation x" can be determined (5 DoF: three-dimensional position plus two angles describing the orientation of x" in a local coordinate system (x', y', z')). In FIG. 10 the arrows 61 orthogonal to x" indicate the unknown orientation of the y" and z" axes. This is the typical situation when the dipole field of a coil is used for localization. While the suspended permanent magnet 3 of the marker device 1 also has a dipole field characteristic, when the magnet 3 oscillates, the plane spanned by the dipole vector motion enables assignment of the missing axis. The direction z" is the direction in which the field strength does not change during the oscillation and the direction of y" follows from x" and z" (cf. FIGS. 11 and 12). A convenient way to implement the six DoF is to separate the measurement of the dipole fields in frequency space. The dynamic dipole moment of the fundamental frequency has an orientation orthogonal to the rotating permanent magnet dipole moment and orthogonal to the oscillation axis. The $2^{nd}$ harmonics (twice the fundamental frequency) dynamic dipole moment has an orientation parallel to the rotating magnets dipole moment and perpendicular to the oscillation axis. With the two distinguishable orthogonal dipoles, the six DoF can be reconstructed.

The marker devices described above with reference to FIGS. 1 to 5 are based on the magneto-mechanical resonance of a permanent magnet. The remanent magnetization of today's permanent magnet materials is very high (NdFeB, $M_R \approx 1.45$ T) and thus enables efficient coupling to externally applied magnetic fields. As a consequence, energy can be efficiently coupled into a resonant mechanical rotational oscillation of a permanent magnet which is either connected to a torsional spring mechanism, for instance, as described above with reference to FIGS. 3 to 5 and/or exposed to a magnetic field of a second permanent magnet, for instance, as described above with reference to FIGS. 1, 2 and 5, to form a high-Q oscillating system. If decoupling from the environment is desired, a counter-oscillating sphere can be employed, for instance, as described above with reference to FIG. 5. The oscillation frequencies are preferentially in a range starting from 100 Hz or a few hundred Hz to 1 kHz or several kHz. The oscillation of the permanent magnet of the marker device creates a time-varying magnetic field that can be detected by electromagnetic induction in a coil system like the coil array 20 described above with reference to FIG. 6.

For the design of the marker device different combinations of the mechanisms exemplarily described above with reference to FIGS. 1 to 5 can be used like using a magnetic field of another permanent magnet and/or using a torsional spring for creating the restoring force which here is a restoring torque. The aim of the marker device is to maximize sensitivity at minimal size. To this end, a high volume of magnetic material as well as a high oscillation frequency is desired. While a purely magnetic marker may be most simple to be built, the combination of a cylindrical oscillating magnet with a spring mechanism, for instance as described above with reference to FIG. 4, may offer the best sensitivity.

The length of the marker capsule, i.e. of the casing of the respective marker device, can be smaller than a millimeter, while still giving enough signal to detect the marker over a distance of up to, for instance, 40 cm. In a preferred embodiment, the diameter of the casing of the marker device is smaller than 0.3 mm, because the marker device can then be integrated into a conventional guidewire typically having a diameter of 0.355 mm. The marker device could also be attached to small implants like stents or directly placed in tissue. Several marker devices operating at different frequencies can be tracked in parallel to determine shape deformation of an object or tissue in a body of a subject.

In order to excite the oscillation in the marker devices, at least one excitation coil is required to produce the excitation field. For 6 DoF localization based on a marker device response signal, an array of coils is required as described above with reference to FIG. 6. Each coil delivers an induction signal that depends on the spatial position and orientation of the coil with respect to the oscillating magnet within the respective marker device. From the known sensitivities of the coils the position and orientation of the dipole can be reconstructed, wherein the fact that the dipole oscillates in a plane enables extraction of the 6 DoF information as illustrated above with reference to FIGS. 10 to 12. Depending on the desired application, the coils can be integrated in, for instance, a mattress on a patient table as illustrated in FIG. 6 or, if a flat form factor is not required, a non-planar set of coils could be placed in a box.

The position and orientation of the respective marker device can either be determined absolutely with respect to a known position and orientation of the coil array like the coil array 20 described above with reference to FIG. 6 or relative with respect to one or several reference marker devices, for instance, if only the mutual distance and orientation between a marked medical device and marked tissue is required. The marker devices could also be made radiopaque to connect the position information directly with x-ray or computed tomography data.

With an additional set of coils like the coils described above with reference to FIG. 8 or by other means like a mechanically actuated set of permanent magnets, dynamic field gradients can be applied to modify the frequency response of the marker devices based on their spatial position. This localization method is independent of the coil-sensitivity-based localization method and can be used to improve localization accuracy. This additional set of coils can comprise at least 6 coils enabling generation of differently orientated local fields and field gradients. From the application of several different field configurations, position and orientation information of the markers can be obtained.

For discriminating several marker devices, their resonant frequencies must be adjusted to have sufficient spectral separation. This adjustment can be carried out, for instance, by adjusting the spring constant accordingly, if the marker device comprises a spring, and/or by modifying the distance of the oscillating magnet to a second magnet if present in the respective marker device. The spectral separation of the resonant frequencies of different marker devices is preferentially larger than 20 Hz, especially if a 10 Hz localization update rate is desired. The excitation pulses can be, for instance, short "delta" pulses timed for in-phase excitation of all oscillating spheres. However, the excitation pulses can also have rather long frequency-selective pulse shapes that can excite several marker devices with sufficient spectral selectivity.

The marker devices can also be used as sensing devices for probing a physical parameter that changes the resonant frequency of the marker device. For instance, an end surface 31 of the marker device like the marker device 1 shown in FIG. 1 might be flexible such that external pressure changes the distance between the two magnets 3 and 4 in FIG. 1. In this case, the position determination unit might not only be adapted to determine the position and optionally also the orientation of the marker device, but can also be adapted to determine the pressure at the determined position of the marker device based on the frequency with which the magnet rotationally oscillates within the respective marker device. For example, in a calibration procedure several frequencies can be assigned to several pressure values and these assignments can be used during an actual pressure measurement for determining the pressure at the determined position of the marker device based on the actually measured frequency of the rotational oscillation within the marker device. The marker device can also be adapted to sense another physical parameter that influences the resonant frequency of the marker device like the radiation.

Figure 13:
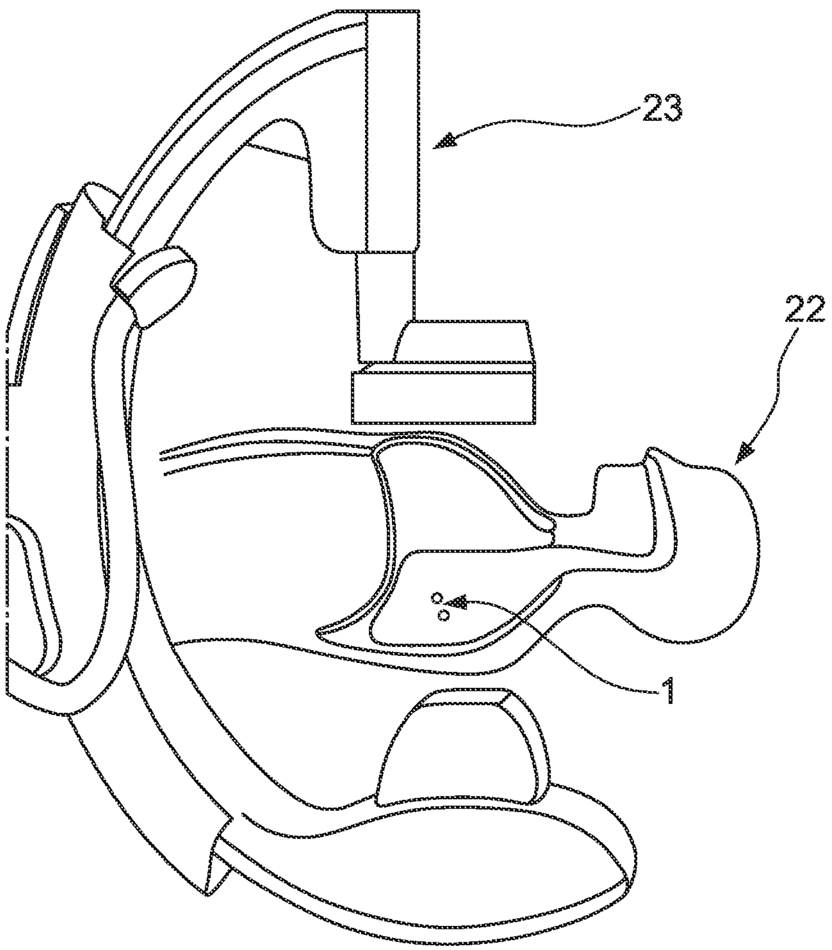
FIG. 13 shows schematically and exemplarily marker devices within a lung of a patient during a surgical procedure.

The marker device can be used for a three-dimensional radiation-free continuous tissue localization in surgery or radiotherapy. FIG. 13 schematically and exemplarily illustrates two marker devices 1 inside a deflated lung of a patient 22.

However, the marker device can also be used for localizing untethered devices inside or outside the body. Several marker devices can be used for wireless shape sensing like determining the shape of catheters and/or guidewires.

One or several marker devices can be used in a minimal invasive lung surgery like in a video assisted thoracoscopic surgery (VATS) lumpectomy. A minimal invasive lung surgery is a treatment to remove pulmonary lung tumors together with a lung segment or lobe. While the localization of lung tumors in a pre-surgical medical image like a computed tomography image is straightforward, during surgery the intervention target is more difficult to localize due to the deflation of the relevant lung parts. For this localization, one or several of the above described magnetic marker devices can be used, wherein this allows localizing the tumor without using x-ray fluoroscopy. These marker devices, which might also be regarded as being "microbots", can be inserted into the tumor either by using a needle based placement or—more advantageously—by injecting them with a catheter based approach into a blood vessel supplying the tumor with blood. Thus, the complete tumor area can be identified based on one or several of the marker devices, wherein the marker devices can be placed in a relatively conservative procedure. The marker devices can be localized in real-time in three dimensions during a thoracoscopic surgery. As explained above, the marker devices can have a diameter being smaller than, for instance, 0.5 mm and they contain a magnetic resonator based on one or several permanent magnets that is excited by an external magnetic field. The oscillation produces a magnetic field that is detected by induction in, for instance, a same set of coils that is used for excitation field generation, i.e., for instance, in the coils 20 described above with reference to FIG. 6. The positions of the marker devices can be overlaid in a video image acquired during thoracoscopic surgery, in order to provide guidance during the surgical procedure.

The marker devices comprise at least one permanent magnet that can perform a rotational oscillation of preferentially at least 30 degrees. In an embodiment, a magnet is attached to a thread that is attracted by a second magnet, for instance, as described above with reference to FIG. 1. Since in this application the marker device is placed or injected in a tumor area, it is not firmly attached to a large mass and the oscillating magnet thus results in a torque on the casing of the marker device and hence on the tissue. In semi-rigid tissue, the energy of the oscillator may hence rapidly deplete. For this reason, at least a second mass with rotational oscillation at the same frequency is present in an embodiment like the embodiment described above with reference to FIG. 5. This second mass cancels the torque on the casing. Preferentially, this second mass is also a magnet to increase the overall magnetization change.

The coils used for exciting the oscillation and generating the induction signals can be arranged in a mat as described above with reference to FIG. 6, wherein the mat may have a size of about 50×50 $cm^2$. This mat may contain, for instance, a 4×4 array of coils. The coils may be made from aluminum or another metal. Such a mat with the coils can locate all marker devices in the lung area simultaneously. However, such a mat may not be suitable for the operation theatre, at least if open surgery is performed. In an embodiment, a smaller handheld version may therefore be used. The handheld version may include the coils to be used for exciting the oscillations and for generating the induction signals, wherein the control of the coils and the tracking is similar to using the coils in the mat, but in the handheld device the number of coils and the size of the coils may be reduced. This handheld device may also contain a display unit. It can also comprise a micro projector or laser projector system that marks the tissue surface spot under which the respective marker device is found. A color code or shape can indicate the depth, for instance, a larger circle can mean a deeper location.

During the surgical procedure in the operation room, the coordinate system of the tracking system is spatially related to an imaging system like the imaging system 23 used during thoracoscopic surgery. This can be done via a direct calibration process. For instance, the positions and optionally orientations of a set of sample marker devices, which are visible for the imaging system which might also be regarded as being a camera system, can be tracked by using the tracking system. It is also possible to attach marker devices to the imaging system itself, in order to track the imaging system by using the tracking system. The registration can also be done in another way, for example, via the imaging space of a hybrid operation room system, i.e. by using tracked surgical instruments and marker device coil array relations to the image space of, for instance, the C-arm system 23. For co-registration in computed tomography planning or C-arm imaging the marker devices can be made radiopaque.

The positions of the marker devices can be presented to the surgeon as an overlay on an image generated by the imaging system like an x-ray CT system used during thoracoscopic surgery.

Due to the selective induction signal generated by using the marker devices, i.e. since the marker devices can have different resonant frequencies such that it is possible to excite only specific marker devices, in case of injection/insertion of the marker devices at a wrong position within the subject, these marker devices at the wrong positions might not be excited during surgery to allow for accurate surgical guidance. For instance, in a pre-operative calibration step the different resonant frequencies of the different marker devices can each be associated to a respective location of the respective marker devices in an x-ray image, wherein the locations of the marker devices in the x-ray image can be used for determining which marker devices have been placed at correct positions within the subject and which marker devices have been positioned at wrong positions within the subject, wherein the tracking control unit 31 can be adapted to control the excitation of the marker devices such that only the marker devices at the correct positions are excited by using the coils 20, wherein the frequencies to be used for exciting the marker devices at the correct positions only can be obtained from the pre-operative calibration.

The tracking system can be adapted to determine the position and preferentially also the orientation of one or several surgical devices, to which marker devices have been attached, relative to the marker devices located at the tumor position. Thus, the position and preferentially also the orientation of one or several surgical devices and the position and optionally also the orientation of the marker devices at the position of the tumor area can be provided in a same frame of reference. The marker devices can comprise a radiopaque marking having a shape or attenuation pattern correlating to the frequency, in order to simplify a position/type identification and in order to avoid the need of a localization system in the pre-operative examination. In other words, in an x-ray image showing the marker devices, marker devices having different resonant frequencies also have different appearances, wherein the relation between the appearances and the resonant frequencies are known. Thus, after a surgeon has identified the marker devices which have been placed at correct positions, due to their appearance in the x-ray image the frequencies for exiting exactly these marker devices are immediately known and the marker devices can be excited accordingly.

Although in above described embodiments the marker devices have been used for marking lung tumors, the marking devices can of course also be used for marking other objects like other kinds of tumors, medical devices as also explained above, or any other object which needs to be tracked.

Although above certain embodiments of marker devices have been described, also other marker devices can be used, which have a casing, a magnetic object and a restoring torque unit being adapted to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque. For instance, also a marker device as described above with reference to FIG. 5 could be used, without the spring 404, wherein in this case the restoring torque is generated by the other magnetic object 405.

Although in above described embodiments the imaging system is preferentially an x-ray C-arm system, also other imaging systems can be used like a C-arm system with an optical camera system, an ultrasound imaging system, for instance, a transesophageal echocardiography (TEE) ultrasound imaging system or an intravascular ultrasound imaging system, et cetera.

The marker device can also comprise means for reducing a possible temperature dependence of the resonant frequency. For instance, the marker device can comprise magnetic material of which the magnetization changes with temperature, in order to thereby change the magnetic field at the location of the magnetic object and hence the resonant frequency with temperature. This magnetic material can be arranged such the change of the resonant frequency with temperature caused by the magnetic material compensates a generally possible change of the resonant frequency due to temperature changes caused by one or several other elements of the marker device. The magnetic material may be located on or adjacent to the further magnetic object. Alternatively or in addition, the magnetic material may be applied to the magnetic object, in order to change its magnetic dipole moment with temperature such that this change of the magnetic dipole moment compensates a generally possible change of the resonant frequency due to temperature changes caused by one or several other elements of the marker device.

The generation of the magnetic field which provides a magnetic torque for rotating the magnetic object of the measurement device out of its equilibrium orientation and for thereby exciting a rotational oscillation of the magnetic object such that it oscillates with the resonant frequency can be implemented in many different ways. For instance, the excitation can use individual single pulses of a magnetic field, wherein between the pulses the frequency and phase of the induced signal can be measured. From this, the timing of the next short pulse can be computed such that it increases the oscillation amplitude of the magnetic object. As an alternative, the single pulse can be replaced with a pulse train of few pulses with positive and negative amplitudes. This short pulse train still covers a relative broad potential excitation spectrum, the center of which is designed to lay approximately at the expected resonant frequency. The timing of the pulse train is again adjusted so that it increases the oscillation amplitude of the magnetic object. The frequency of the resulting optimized induction signal can be regarded as being the resonant frequency.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the position and preferentially also the orientation of a marker device based on the generated induction signals, the control of the excitation of the marker devices by controlling the current within the coils, et cetera, performed by one or several units or devices can be performed by any other number of units or devices. These procedures and/or the control of the tracking system in accordance with the tracking method and/or the control of the guidance system in accordance with the guidance method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a marker device and a tracking system for tracking the marker device, wherein the marker device comprises a rotationally oscillatable magnetic object and wherein the rotational oscillation is excitable by an external magnetic field, i.e. a magnetic field which is generated by a magnetic field providing unit that is located outside of the marker device. The rotational oscillation of the magnetic object induces a current in coils, wherein based on these induced currents the position and optionally also the orientation of the marker device is determined. This wireless kind of tracking can be carried out with relatively small marker devices, which can be placed, for instance, in a guidewire, the marker devices can be read out over a relatively large distance and it is possible to use a single marker device for six degrees of freedom localization.

The invention claimed is:

1. A marker device to be tracked, the marker device comprising:

a casing;

a magnetic object arranged within the casing, wherein the magnetic object is rotatable around a rotational axis centrally traversing the magnetic object in response to an external magnetic torque acting on the magnetic object; and a further magnetic object, wherein the magnetic object and the further magnetic object are permanent magnets, wherein a direction of a magnetic moment of at least one of the magnetic object or the further magnetic object is perpendicular to the rotational axis;

wherein the magnetic moment of the magnetic object and the magnetic moment of the further magnetic object are arranged in opposite directions, and wherein the further magnetic object is either directly connected to or connected via a torsional spring to the casing.

2. The marker device of claim 1, wherein the marker device has a cylindrical shape and an outer diameter smaller than 1 mm.

3. The marker device of claim 1, wherein a resonant oscillation of the magnetic object and a resonant oscillation of the further magnetic object comprise a similar or same frequency, and wherein the resonant oscillation of the magnetic object and the resonant oscillation of the further magnetic object comprise a phase difference.

4. The marker device of claim 1, further comprising a filament.

5. The marker device of claim 4, wherein the filament is adapted to prevent the magnetic object from touching the further magnetic object.

6. The marker device of claim 1, wherein the marker device is configured to operate under at least one of the following characteristics:

a Q factor of at least 100, a dynamic dipole moment of at least 0.5 μAm2, or a resonant frequency of at least 100 Hz.

7. The marker device of claim 1, wherein the marker device is adapted to operate under frequencies ranging from 100 Hz to 2 kHz.

8. The marker device of claim 1, wherein the further magnetic object is stationarily attached to the casing.

9. A marker device to be tracked, the marker device comprising:

a casing;

a magnetic object arranged within the casing, wherein the magnetic object is rotatable around a rotational axis centrally traversing the magnetic object in response to an external magnetic torque acting on the magnetic object; and a further magnetic object, wherein the magnetic object and the further magnetic object are permanent magnets, wherein a direction of a magnetic moment of at least one of the magnetic object or the further magnetic object is perpendicular to the rotational axis;

wherein the magnetic moment of the magnetic object and the magnetic moment of the further magnetic object are arranged in opposite directions, wherein the magnetic object is connected to the casing via a filament, and wherein the further magnetic object is fixedly attached to the casing.

10. The marker device of claim 1, wherein at least one of the torsional spring or the magnetic object is adapted to provide a restoring torque.

11. A medical device, comprising:

one or more of: a catheter, a guidewire, or an implant; and the marker device of claim 1.

* * * * *